(12) United States Patent
Muthusamy et al.

(10) Patent No.: US 8,945,622 B2
(45) Date of Patent: Feb. 3, 2015

(54) SUSTAINED RELEASE COMPOSITION OF THERAPEUTIC AGENT

(75) Inventors: Ramesh Muthusamy, Maharashtra (IN); Mohan Gopalkrishna Kulkarni, Maharashtra (IN)

(73) Assignee: Council of Scientific And Industrial Research, New Delhi (IN)

( * ) Notice: Subject to any disclaimer, the term of this patent is extended or adjusted under 35 U.S.C. 154(b) by 312 days.

(21) Appl. No.: 13/254,712

(22) PCT Filed: Mar. 5, 2010

(86) PCT No.: PCT/IB2010/000459
§ 371 (c)(1),
(2), (4) Date: Jan. 13, 2012

(87) PCT Pub. No.: WO2010/103365
PCT Pub. Date: Sep. 16, 2010

(65) Prior Publication Data
US 2012/0107400 A1 May 3, 2012

(30) Foreign Application Priority Data
Mar. 9, 2009 (IN) .............................. 453/DEL/2009

(51) Int. Cl.
| A61K 47/38 | (2006.01) |
| A61K 47/34 | (2006.01) |
| A61K 9/28 | (2006.01) |
| A61K 31/167 | (2006.01) |
| A61K 31/192 | (2006.01) |
| A61K 31/522 | (2006.01) |
| A61K 31/545 | (2006.01) |
| A61K 31/554 | (2006.01) |

(52) U.S. Cl.
CPC .............. *A61K 47/34* (2013.01); *A61K 9/2853* (2013.01); *A61K 31/167* (2013.01); *A61K 31/192* (2013.01); *A61K 31/522* (2013.01); *A61K 31/545* (2013.01); *A61K 31/554* (2013.01)
USPC ....................................................... 424/482

(58) Field of Classification Search
None
See application file for complete search history.

(56) References Cited

U.S. PATENT DOCUMENTS

| 4,863,744 | A |   | 9/1989 | Urquhart et al. |
| 4,968,508 | A |   | 11/1990 | Oren et al. |
| 5,280,089 | A | * | 1/1994 | DeGraaf et al. .............. 525/445 |
| 5,422,123 | A |   | 6/1995 | Conte et al. |
| 5,449,707 | A |   | 9/1995 | Higashiura et al. |
| 5,945,125 | A |   | 8/1999 | Kim |
| 6,274,173 | B1 |   | 8/2001 | Sachs et al. |
| 6,312,724 | B1 |   | 11/2001 | Odidi et al. |
| 6,486,213 | B1 | * | 11/2002 | Chen et al. ................. 514/772.1 |
| 6,569,457 | B2 |   | 5/2003 | Ullah et al. |
| 6,893,661 | B1 |   | 5/2005 | Odidi et al. |
| 2003/0190362 | A1 |   | 10/2003 | Sackler |
| 2005/0191349 | A1 |   | 9/2005 | Boehm et al. |
| 2008/0026060 | A1 |   | 1/2008 | Zerbe et al. |

FOREIGN PATENT DOCUMENTS

| WO | 9748386 A1 | 12/1997 |
| WO | 9932091 A1 | 7/1999 |
| WO | 0234240 A2 | 5/2002 |
| WO | 03099203 A2 | 12/2003 |
| WO | 2004091583 A1 | 10/2004 |
| WO | 2005030179 A1 | 4/2005 |
| WO | 2007052877 A1 | 5/2007 |
| WO | 2007143290 A2 | 12/2007 |

OTHER PUBLICATIONS

International Search Report dated Sep. 30, 2010 for PCT application No. PCT/IB2010/000459.
Written Opinion dated Sep. 30, 2010 for PCT application No. PCT/IB2010/000459.

* cited by examiner

*Primary Examiner* — Brian Gulledge
(74) *Attorney, Agent, or Firm* — Ohlandt, Greeley, Ruggiero & Perle, LLP

(57) ABSTRACT

A pH dependent drug delivery system comprising a pH sensitive graft copolymer, a therapeutically active agent and other pharmaceutically acceptable ingredients. More specifically, a composition which is capable of suppressing the drug release in the acidic pH prevalent in the stomach and releasing the drug over an extended period of time at pH prevalent in the intestinal region.

27 Claims, 5 Drawing Sheets

SUSTAINED RELEASE COMPOSITION OF THERAPEUTIC AGENT

The following specification particularly describes the invention and the manner in which it is to be performed:

FIELD OF THE INVENTION

The present invention relates to sustained release composition for oral administration comprising a graft copolymer which exhibits pH dependent behavior, a therapeutically active agent and pharmaceutically acceptable ingredients.

The present invention further relates to relates to an oral delivery of therapeutic agent, particularly pH dependent drug delivery system which is capable of releasing a drug over an extended period of time at pH prevalent in the intestinal region and suppressing the release of pH prevalent in the stomach.

BACKGROUND OF THE INVENTION

Drugs with shorter half-life require to be provided in sustained release dosage forms to avoid multiple dosing in a day, which usually affects patient compliance. Such dosage forms should be designed in such a way that they reach the right place at right time in effective form. Polymers of natural and synthetic origins have been used extensively to modify release rate of drugs. Amongst other factors, drug loading and its solubility, the polymer swelling and dissolution behaviour in the body fluid influence the drug release rate. The pH independent polymers like hydroxypropyl methyl cellulose, polyethylene oxide, ethylcellulose, carboxymethyl cellulose and guar gum are the polymers most widely used to obtain sustained release dosage forms.

References may be made to U.S. Pat. No. 6,312,724, wherein a sustained release formulation of diclofenac sodium using hydroxyethyl cellulose prepared by direct compression method is disclosed.

References may be made to U.S. Pat. No. 5,945,125, wherein a preparation of controlled release tablet using polyethylene oxide as water swellable polymer is disclosed and showed the zero order release of incorporated drug.

References may be made to U.S. Pat. No. 5,422,123, wherein a tablet composition with zero order release behaviour has been disclosed. The tablet comprises a gelling polymer in the core and is partially covered with supporting layer of polymer which is slowly soluble in aqueous medium.

Sustained release formulations based on pH independent hydrophilic polymers deliver the drug depending on drug solubility at pH of the physiological medium. This leads to dose dumping at particular site in the gastrointestinal tract wherein the drug is highly soluble. There are many drugs which benefit from prohibiting their release in the stomach for example, the drugs which undergo degradation at acidic pH, the drugs which create gastric inflammation and the drugs which induce nausea and vomiting. These types of drugs need to be formulated in such way that the dosage form should suppress drug release in the stomach and release it slowly along the intestinal tract. This could be possible by formulating the drug using pH dependent anionic polymers as they are insoluble at acidic pH prevalent in the stomach and soluble in near neutral pH prevalent in the intestine. Currently available polymers like cellulose acetate phthalate, cellulose acetate trimellitate, hydroxypropyl methylcellulose phthalate, hydroxypropyl methyl cellulose acetate succinate, polyvinyl acetate phthalate and Eudragit L are insoluble at acidic pH. However they dissolve rapidly at near neutral and alkaline condition.

References may be made to Journal "O. S. Silva, C. R. F. Souza, W. P. Oliveira and S. C. S. Rocha, Drug Development and Industrial Pharmacy, 32, 661-667, 2006" wherein the release behaviour of Eudragit L-30D-55 coated diclofenac sodium granules is described. The drug, microcrystalline cellulose and polyvinylpyrrolidone K-30 were wet granulated and then coated with pH sensitive polymer Eudragit L-30D-55. The coated granule did not release the drug at acidic pH and released it rapidly at near neutral pH.

The rapid dissolution at near neutral pH renders these polymers unsuitable for the development of sustained release formulation even though they could maintain integrity at acidic pH. These polymers are being used as an enteric coating for the dosage forms wherein the drug release is to be avoided in the stomach.

References may be made to patent application WO 03099203 A2, wherein Gonzales Gilbert et al. disclosed an enteric coated caffeine delivery system. The drug containing core was coated with pH sensitive polymer dispersion Eudragit L100-55. The system comprised a seal coat of hydrophilic polymer like hydroxypropyl methyl cellulose between the core and an enteric coat. It has been claimed that the formulations did not release the drug in stomach and released the same rapidly in intestine. This would avoid the irritation in the stomach often caused by the caffeine if it were to be released in stomach.

Similarly, the drugs which rapidly undergo degradation at acidic pH of the stomach must be protected within the dosage forms. For example, didanosine is an acid labile drug which should be protected in the stomach before it is delivered in the intestine. References may be made to U.S. Pat. No. 6,569,457, wherein a didanosine composition coated with an enteric polymer Eudragit L-30D-55 is reported. The formulation was claimed to be intact at acidic pH condition and protect the drug from degradation and release the content rapidly at near neutral pH.

References may be made to Journal "Giovanni Filippo Palmieri, Simona Michelini, Piera Di Martino and Sante Martelli, Drug Development and Industrial Pharmacy, 26, 837-845, 2000" wherein enteric polymer for the development of sustained release formulations is described. Paracetamol tablets were prepared using various enteric polymers such as cellulose acetate phthalate, cellulose acetate trimellitate, hydroxypropylmethylcellulose phthalate, Eudragit L and Eudragit S. The tablets were prepared by direct compression and microsphere compression methods. It was reported that the directly compressed tablets exhibited neither enteric property, nor sustained release of paracetamol. The microsphere compressed tablets comprising cellulose acetate phthalate, cellulose acetate trimellitate, hydroxypropylmethylcellulose phthalate and Eudragit S exhibited enteric property and sustained release of drug when the drug and polymer ratio was 1:8. However, Eudragit L based formulation exhibited neither enteric property nor sustained release of drug.

Currently, the sustained release of drug in the intestinal region has been achieved by using combination of pH independent and pH dependent polymers.

References may be made to U.S. Pat. No. 4,863,744 wherein system comprised drug loaded tiny reservoirs coated with pH independent polymer placed within pH sensitive anionic polymer is reported. The integrity of dosage form at pH 3.5 was facilitated by the pH sensitive anionic polymer coating. Upon dissolution of this coating at near neutral condition, the tiny reservoirs were exposed to the medium and released the drug over an extended period of time.

References may be made to patent application WO 2005/030179 A1, wherein Cho et al. developed a sustained release composition of cardiovascular drug. The formulation was designed to control the initial burst release of drug. A tablet comprising a drug and a pH independent hydrophilic polymer was coated with an enteric polymer. An additional drug layer comprising a pH independent or pH dependent polymer was provided over the enteric coat.

References may be made to U.S. Pat. No. 4,968,508, wherein Oren et al. disclosed a sustained release composition comprising a basic drug which is highly soluble at acidic pH prevalent in stomach. The formulation comprised a core tablet loaded with drug and a hydrophilic polymer which was then coated with an enteric polymer. It was claimed that the formulation suppressed the drug release in the stomach and sustained release in intestinal region.

References may be made to U.S. Pat. No. 6,893,661 A1, wherein Odidi et al. disclosed a controlled release formulation. It comprised a drug and combination of hydrophilic and hydrophobic polymer in the form of a tablet. In order to impart stealth characteristics to the tablet, so as to avoid dose dumping and food effects in the stomach, the tablet was coated with an enteric polymer.

Drugs which undergo degradation under the acidic environment of stomach need to be protected within the dosage form. Proton pump inhibitors are used to control gastric acid secretion which often leads to diseases like gastric and duodenal ulcer. References may be made to patent application EP 1043976 B1, wherein Karehill et al. disclosed an extended release dosage form of proton pump inhibitors. The drug containing granules was prepared by using a pH independent hydrophilic or hydrophobic polymer and compressed in to a tablet. The tablet was coated with an enteric polymer. An optional coat between the drug core and the enteric coat was provided.

References may be made to U.S. Pat. No. 6,274,173 B1, wherein delayed release dosage form comprising a proton pump inhibitor was disclosed for the treatment of gastric disorders is mentioned. The dosage form was prepared by granulating the drug and other ingredients to form a tablet. A release retarding layer of pH independent polymer and an enteric coating was applied on the tablet.

References may be made to US patent application 2008/0026060 A1, wherein Zerbe et al. disclosed a controlled release composition of antidepressant drug bupropion in combination with smoking cessation aid like mecamylamine. The delivery system was developed by formulating granules of stabilized bupropion and hydroxyalkyl cellulose with mecamylamine. The granule was dispersed in a sustained release polymer and then compressed into a tablet. The coating of above tablet with an enteric polymer enhanced the stability of bupropion on storage.

Non-steroidal anti-inflammatory drugs (NSAID) are known to cause gastric irritation and bleeding when they released in stomach. An ideal dosage form containing NSAID should delay the drug release until it reaches intestine. References may be made to patent application WO02/34240 A2, wherein such a delayed and sustained release composition of NSAID was disclosed for the pain management. The dosage form comprises an inert pellet such as non-peril seeds coated by a layer containing the drug followed by a rate controlling layer of water insoluble polymer and finally an enteric polymer layer.

There are some drugs which cause nausea and vomiting when released in stomach. Paroxetine is such a drug being used for the treatment of depression. Delivery systems for this kind of drug have to be designed in such a way that the drug release does not take place in the stomach and release over an extended time period takes place in the intestine. References may be made to patent application WO 2007/052877, wherein Kim et al. disclosed such a formulation which is a tablet comprising a drug and pH independent hydrophilic polymer like hydroxypropyl methyl cellulose coated with an enteric polymer. A seal coat was provided to avoid the interaction between the drug in the core and enteric polymer.

Venlafaxine is an antidepressant drug with shorter half-life and a once daily dosage form which avoids multiple dosing in a day is highly desirable. The problem associated with this drug is side effects such as nausea and emesis when the drug is released in the stomach. References may be made to patent application WO 2007/143290 A2, wherein venlafaxine composition disclosed by Vishnupad in provides an extended release of drug after a predetermined time lag. The dosage form is a compressed core comprising drug and a pH independent hydrophilic polymer coated with a combination of water insoluble polymer and an enteric polymer.

Disorders associated with post awakening period in the morning have to be treated with once daily bedtime dosage forms to enhance the patient compliance. Such dosage form should delay the drug release after ingestion and then release the content over extended period time so as to maintain the effective plasma concentration in the morning. References may be made to patent application WO 2004/091583 A1, wherein Mehta disclosed such a chrono delivery formulation for the treatment of early morning pathologies such as arthritis, angina, atrial fibrillation and hypertension. The dosage form comprised a core coated with a drug layer followed by multiple numbers of layers one over another in the sequence of seal coat of water soluble polymer, a rate controlling layer of water insoluble polymer and an enteric polymer.

References may be made to patent application WO97/48386, wherein Chen disclosed a once daily formulation of cardiovascular drug diltiazem hydrochloride. The tablet comprised a drug and pH independent hydrophilic polymer like hydroxypropyl methyl cellulose. The tablet was given an enteric coating to avoid the drug release in stomach which would result in higher plasma concentration of drug at earlier stage. It is evident from the above disclosures that the pH independent hydrophilic polymer can not suppress the drug release under the acidic condition of stomach. This leads to dose dumping and initial burst release of the drug, especially when drug is highly soluble at acidic pH of the stomach. Also some drugs should not be released within the stomach as they induce gastric inflammation or undergo degradation. Still some other drugs have to be delivered after a delay time for the treatment of chronic diseases. The currently available pH sensitive polymers do not provide sustained release of drug in intestine apart from eliminating the release under acidic environment of stomach. It is well known that dosage forms which offer pH dependent drug release are necessary for the treatment of many diseases.

Currently this has been achieved by using a combination of pH independent hydrophilic or hydrophobic polymers and a pH sensitive polymer. Therefore there is a need for pH dependent drug delivery system which does not require multiple numbers of polymers and multilayered construction. This will make processing the preparation of dosage forms easier. The present invention provides formulations which suppress the drug release at pH prevalent in the stomach and releases over an extended period of time at pH prevalent in the intestinal region.

OBJECTIVE OF THE INVENTION

The main objective of the present invention is to provide pH dependent sustained release composition.

Another objective of the present invention is to provide pH dependent sustained release composition comprising a pH sensitive graft copolymer (P), a therapeutically active agent and pharmaceutically acceptable ingredients.

Another objective of the present invention is to provide pH dependent sustained release composition which suppresses the drug release at pH prevalent in the stomach and releases over an extended period of time at pH prevalent in the intestinal region.

SUMMARY OF THE INVENTION

Accordingly present invention provides a sustained release composition for oral administration comprising:
(a) a graft copolymer which exhibits pH dependent behavior having the formula 1

$$P\ [A_{(x)}\ B_{(y)}\ C_{(z)}]\ |\ (D)_w$$

Formula 1 comprises of:
  i. a backbone having the formula $P\ [A_{(x)}B_{(y)}C_{(z)}]$ comprising a diol (A), a dicarboxylic acid or acid anhydride (B) and a monomer containing pendent unsaturation (C)
    wherein (x)=39-46%, (y)=49-54% (z)=5-8% by mole;
  ii. a graft which is a polymer of the acidic monomer (D) which comprises 'w' weight percent of the total weight of the said graft copolymer such that 'w' is 34-55%.
(b) a therapeutically active agent; and
(c) pharmaceutically acceptable ingredients.

In an embodiment of the present invention, the backbone is poly (ester-ether) or polyester.

In another embodiment of the present invention, the diol is selected from the group consisting of aliphatic diol, cycloaliphatic diol and aromatic diol.

In yet another embodiment of the present invention, the aliphatic diol is selected from the group consisting of diethylene glycol, triethylene glycol, tetraethylene glycol, dipropylene glycol, tripropylene glycol, polyethylene glycol ($M_n$~200), polyethylene glycol ($M_n$~400), polyethylene glycol ($M_n$~1000), polyethylene glycol ($M_n$~2000), 1,2-ethane diol, 1,3-propane diol, 1,2-propane diol, 2-methyl-1,3-propane diol, 1,4-butane diol, 1,3-butane diol, 1,2-butane diol, 1,5-pentane diol, 1,6-hexane diol, 1,7-heptane diol, 1,8-octane diol, 1,9-nonane diol and 1,12-dodecane diol.

In yet another embodiment of the present invention, the cycloaliphatic diol is 1,4-cyclohexanedimethanol.

In yet another embodiment of the present invention, the aromatic diol is bis(2-hydroxyethyl) terephthalate.

In still another embodiment of the present invention, the dicarboxylic acid is selected from the group consisting of succinic acid, glutaric acid, adipic acid, pimelic acid, suberic acid, azelaic acid, sebacic acid and dodecanedioic acid.

In still another embodiment of the present invention, the acid anhydride is selected from succinic anhydride and phthalic anhydride.

In yet another embodiment of the present invention, the monomer containing pendent unsaturation is an epoxy monomer or a diol monomer.

In yet another embodiment of the present invention, the epoxy monomer is selected from glycidyl methacrylate and glycidyl acrylate.

In yet another embodiment of the present invention, the diol monomer is selected from trimethylolpropane monomethacrylate and trimethylolpropane monoacrylate.

In yet another embodiment of the present invention, the acidic monomer is a carboxylic acid selected from acrylic acid and methacrylic acid.

In yet another embodiment of the present invention, the therapeutically active agent is selected from, but not limited to the group consisting of anti-inflammatory drugs, cardiovascular drugs, antibiotic drugs, analgesic drugs and anti-asthmatic drugs.

In yet another embodiment of the present invention, the anti-inflammatory drug is selected from the group consisting of ibuprofen, ketoprofen, indomethacin, diclofenac and naproxen.

In yet another embodiment of the present invention, the cardiovascular drug is selected from the group consisting of verapamil, nifedepine, captopril, propranolol, atenolol and diltiazem.

In yet another embodiment of the present invention, the antibiotic drug is selected from ampicillin and cephalexin.

In yet another embodiment of the present invention, the analgesic drug is selected from the group consisting of acetylsalicylic acid, acetaminophen, oxycodone and morphine.

In yet another embodiment of the present invention, the anti-asthmatic drug is selected from the group consisting of aminophylline, theophylline and salbutamol.

In yet another embodiment of the present invention., pharmaceutically acceptable ingredients are selected from, but not limited to the group consisting of filler, binder, lubricant and glidant.

In yet another embodiment of the present invention., filler is selected from microcrystalline cellulose and lactose monohydrate, binder is selected from hydroxypropyl methyl cellulose and polyvinylpyrrolidone, lubricant is selected from magnesium stearate and talc and glidant is aerosil.

In yet another embodiment of the present invention, the pH sensitive graft copolymer comprises 20-50% of the total weight of the formulation.

In yet another embodiment of the present invention, the therapeutically active agent comprises 20-40% of the total weight of the formulation.

In yet another embodiment of the present invention, the pharmaceutically acceptable ingredients comprise 15-40% of the total weight of the formulation.

In yet another embodiment of the present invention., pharmaceutically acceptable ingredients comprise filler 10-30%, a binder 5-10%, a lubricant 0.5-2% and a glidant 0.2-1% of the total weight of the formulation.

In yet another embodiment of the present invention, the sustained release composition is produced in pharmaceutical solid dosage form.

In yet another embodiment of the present invention, the dosage form comprises an optional coat of said pH sensitive graft copolymer.

In yet another embodiment of the present invention., process for the preparation of the sustained release composition comprises the steps of:
  I. dry granulating and mixing the therapeutically active agent, pH sensitive graft copolymer and pharmaceutically acceptable ingredients to obtain granular mixture;

II. compressing the granular mixture as obtained in step (I) into tablet to obtain core tablet;

III. dissolving pH sensitive graft copolymer and di-n-butyl phthalate in solvent mixture to obtain 10% solution;

IV. coating the core tablet as obtained in step (II) with 10% solution of the pH sensitive graft copolymer and plasticizer as obtained in step (III) to obtain coated tablet;

V. drying the coated tablet as obtained in step (IV) to obtain sustained release composition for oral administration.

DETAILED DESCRIPTION OF THE INVENTION

Figure 1:
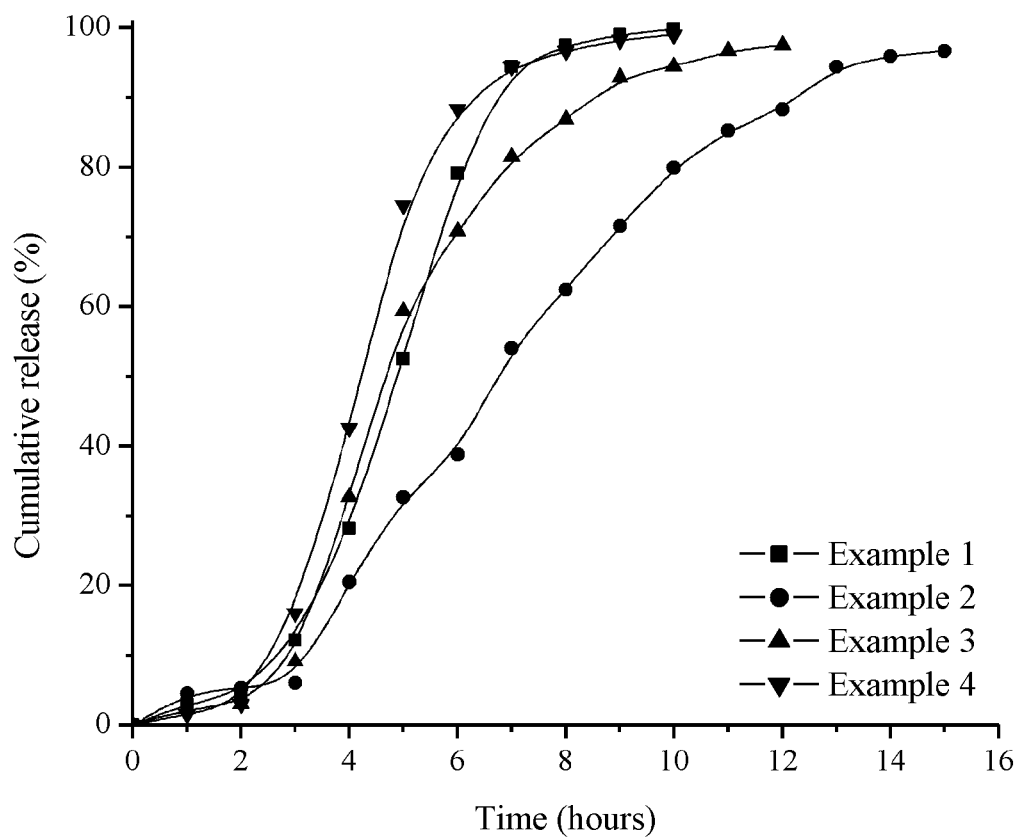
FIG. 1. Release profile of diclofenac sodium sustained release formulations.
Figure 2:
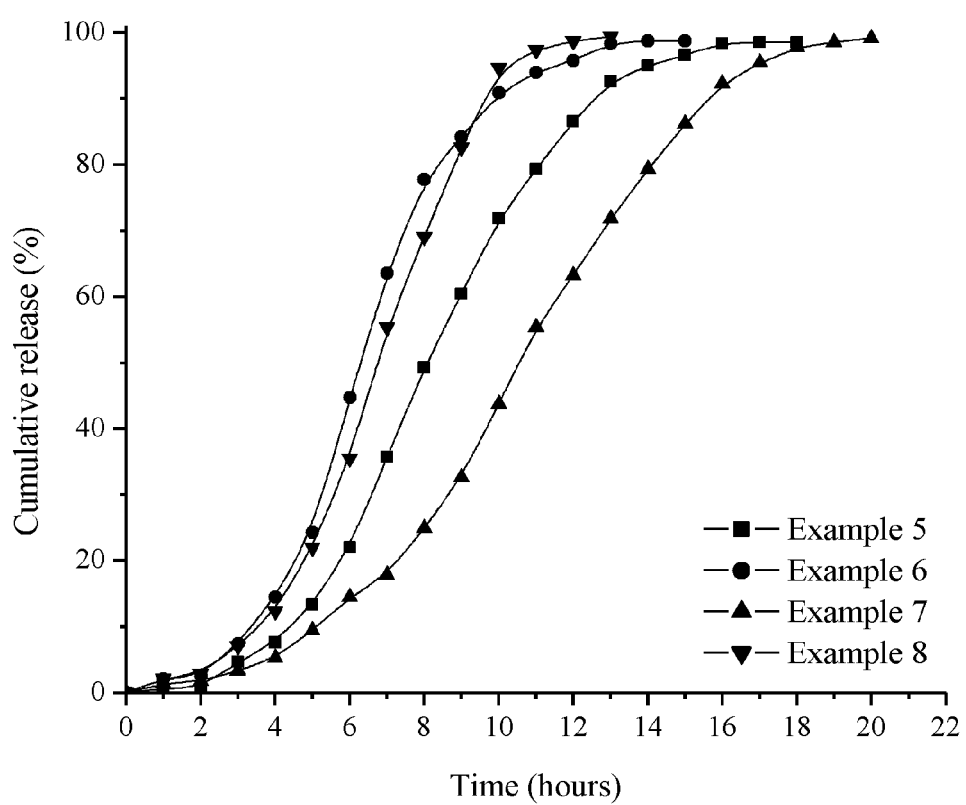
FIG. 2. Release profile of diltiazem hydrochloride sustained release formulations.
Figure 3:
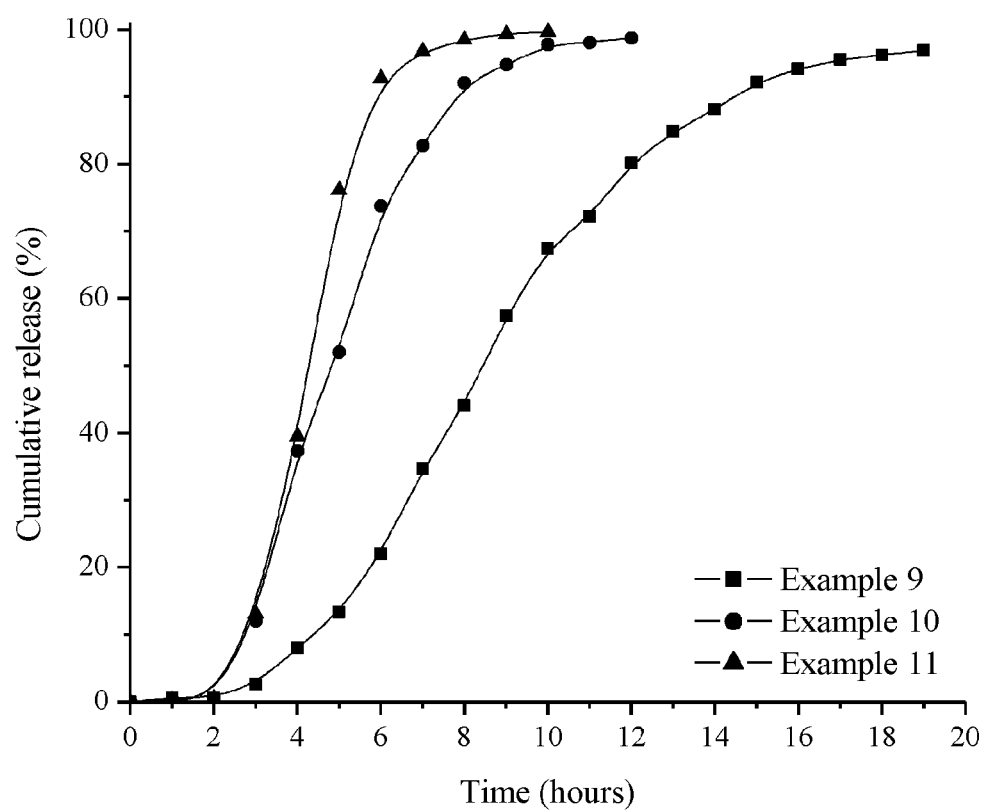
FIG. 3. Release profile of theophylline sustained release formulations.
Figure 4:
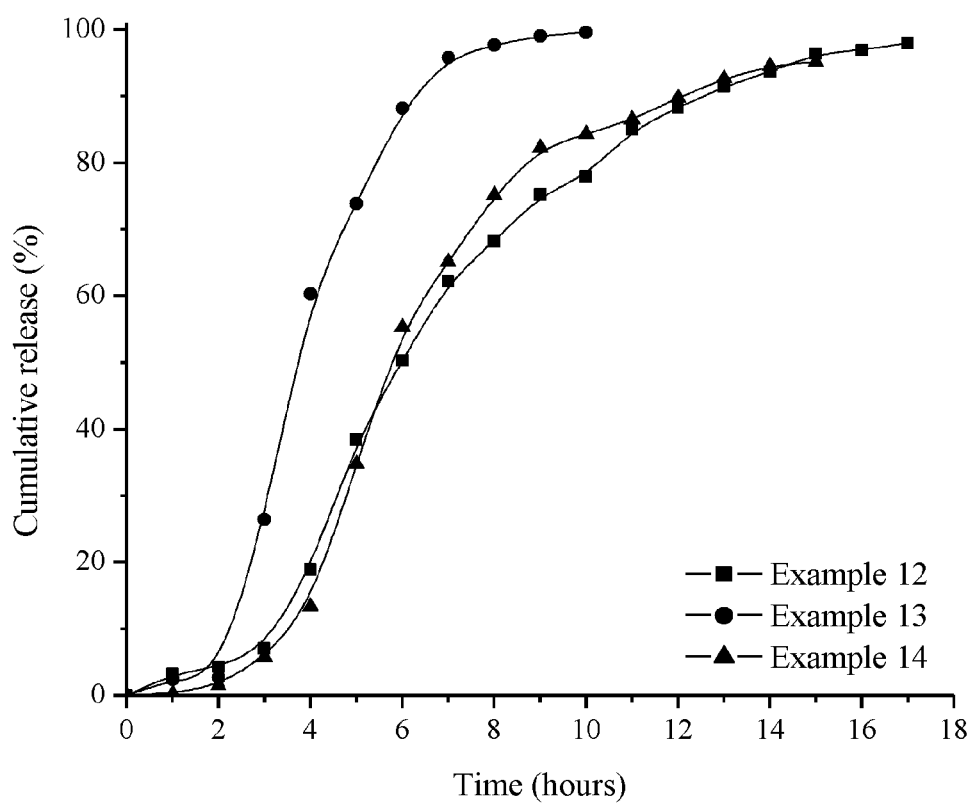
FIG. 4. Release profile of acetaminophen sustained release formulations.
Figure 5:
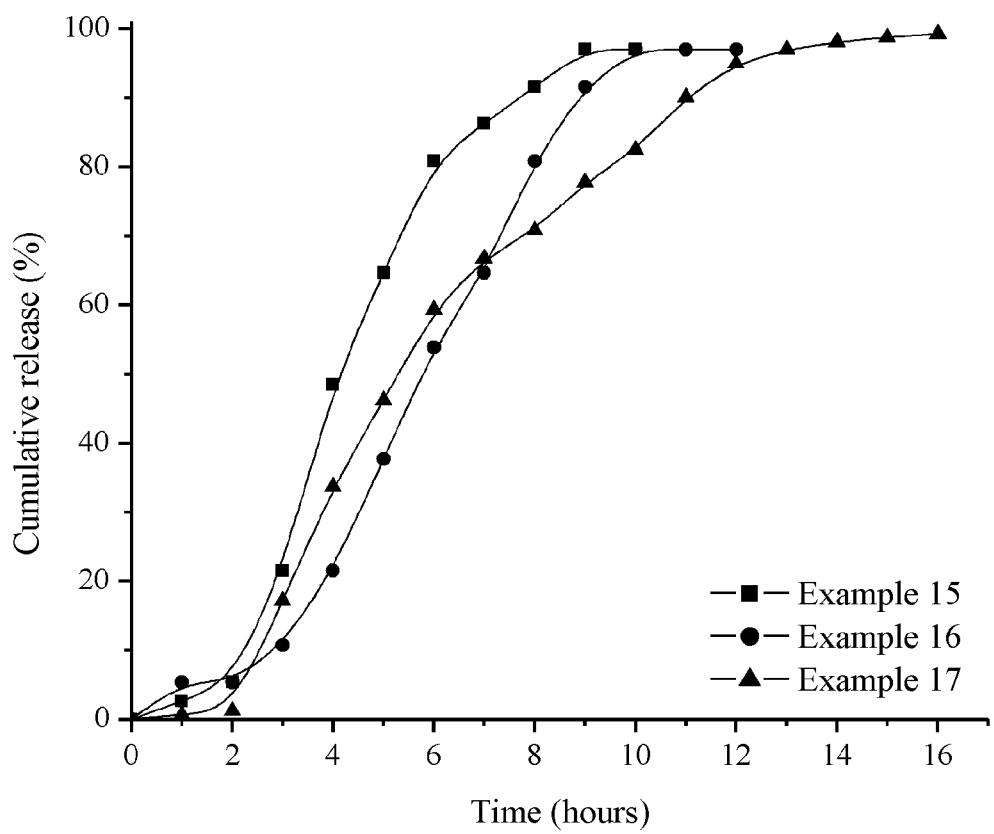
FIG. 5. Release profile of cephalexin monohydrate sustained release formulations.

The present invention provides a pH dependent sustained release composition which comprises;

(a) A graft copolymer which exhibits pH dependent behaviour having the formula 1

Formula 1 which comprises;

(i) a backbone having the formula $P[A_{(x)}B_{(y)}C_{(z)}]$ comprising (A) a diol, (B) a dicarboxylic acid or acid anhydride and (C) a monomer containing pendent unsaturation wherein (x)=39-46%, (y)=49-54% (z)=5-8% by mole; and (ii) a graft which is a polymer of the acidic monomer (D) which comprises 'w' weight percent of the total weight of the said graft copolymer such that 'w' is 34-55%.

(b) a therapeutically active agent; and (c) pharmaceutically acceptable ingredient.

The backbone is polyester or poly (ester-ether).

The diol (A) is selected from the group comprising aliphatic diol, cycloaliphatic diol and aromatic diol. The aliphatic diol is selected from diethylene glycol, triethylene lycol, tetraethylene glycol, dipropylene glycol, tripropylene glycol, polyethylene glycol $M_n\sim200$, polyethylene glycol $M_n\sim400$, polyethylene glycol $M_n\sim1000$, polyethylene glycol $M_n\sim2000$, 1,2-ethane diol, 1,3-propane diol, 1,2-propane diol, 2-methyl-1,3-propane diol, 1,4-butane diol, 1,3-butane diol, 1,2-butane diol, 1,5-pentane diol, 1,6-hexane diol, 1,7-heptane diol, 1,8-octane diol, 1,9-nonane diol and 1,12-dodecane diol. The cycloaliphatic diol is 1,4-cyclohexanedimethanol. The aromatic diol is bis(2-hydroxyethyl) terephthalate.

The dicarboxylic acid or acid anhydride (B) is selected from succinic acid, glutaric acid, adipic acid, pimelic acid, suberic acid, azelaic acid, sebacic acid, dodecanedioic acid, succinic anhydride and phthalic anhydride.

The monomer containing pendent unsaturation (C) is selected from glycidyl methacrylate, glycidyl acrylate, trimethylolpropane monomethacrylate and trimethylolpropane monoacrylate.

The acidic monomer (D) is selected from acrylic acid and methacrylic acid.

The sustained release composition comprises therapeutically active agent selected from, but not limited to the group consisting of anti-inflammatory drugs such as ibuprofen, ketoprofen, indomethacin, diclofenac and naproxen, cardiovascular drugs such as verapamil, nifedepine, captopril, propranolol, atenolol and diltiazem, antibiotic drugs such as ampicillin and cephalexin, analgesic drugs such as acetylsalicylic acid, acetaminophen, oxycodone and morphine, antiasthmatic drugs such as aminophylline, theophylline and salbutamol.

The sustained release composition also comprises pharmaceutically acceptable ingredients which include, but not limited to filler, binder, lubricant and glidant. The sustained release composition is in the oral dosage form such as tablets, pills, capsules or granules. In one of the embodiment the compositions are in the form of tablets. The sustained release composition comprises at least one said pH sensitive graft copolymer in the range of 20-50%, therapeutically active agent comprises 20-40%, and the pharmaceutically acceptable ingredients comprise 15-40% of the total weight of tablet. The said pharmaceutically acceptable ingredients comprise; a filler 10-30% (e.g., microcrystalline cellulose, lactose monohydrate), a binder 5-10% (e.g., Hydroxypropyl methyl cellulose 5 Cps, polyvinylpyrrolidone K 30), a lubricant 0.5-2% (e.g., Magnesium stearate, talc) and a glidant 0.2-1% (e.g., aerosil) of the total weight of tablet.

The sustained release composition was prepared by dry granulation of drug, pH sensitive graft copolymer, filler and binder. To this a lubricant and glidant were added and mixed thoroughly. The obtained granular mixture was compressed into tablet. The tablet comprises an optional coat of any one of said pH sensitive graft copolymers. For instance, in one sustained release composition the pH sensitive graft copolymer in the coat was same as in the core. In another case the pH sensitive graft copolymer in the coat was different from that in the core. The coating composition also comprised a plasticizer 10% (e.g., di-n-butyl phthalate) on the weight of said coat. In one aspect of the invention, a sustained release composition which eliminates or suppresses the drug release at pH prevalent in the stomach and releases over an extended period of time at pH prevalent in the intestine region is provided.

In another aspect of the invention, a sustained release composition which is capable of protecting the drug from the acidic environment prevalent in the stomach is provided.

In another aspect of the invention, a sustained release composition which does not induce the gastric inflammation is provided. In yet another aspect of the invention, a pH dependent sustained release composition which does not require more than one polymer to obtain the said release profile is provided.

In the examples the diol, dibasic acid, unsaturated monomer and acidic monomer are described by the following abbreviations.

1,4 BD—1,4 Butane diol, DEG—Diethylene glycol, 1,4 CD—1,4 Cyclohexane dimethanol, BHET—bis(2-hydroxyethyl) terephthalate, SA—Succinic acid, SEB—Sebasic acid, AA—Adipic acid, DDA—Dodecanedioic acid, PA—Phthalic anhydride, GMA—Glycidyl methacrylate, TMPMA—Trimethylolpropane monomethacrylate, MAA—Methacrylic acid.

The synthesis of pH sensitive graft copolymers based on the above monomers is described in our co pending application 0452DEL2009 which is included herein fully as reference.

The following examples are given by way of illustration only and therefore should not be construed to limit the scope of the present invention.

EXAMPLE 1

This example describes the preparation and the dissolution profile of sustained release diclofenac sodium tablet comprising the pH sensitive graft copolymer

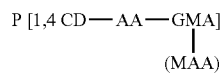

in the core and coat wherein the MAA content is 43 wt. %.

(I) Preparation of Sustained Release Tablet (a) Preparation of Core Tablet

The drug diclofenac sodium, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 8.0 mm in diameter. The composition of tablet is given in Table 1.

TABLE 1

Composition of diclofenac sodium sustained release tablet

| Core tablet composition | Weight (mg) |
| --- | --- |
| Diclofenac sodium | 100.00 |
| Graft copolymer | 57.50 |
| Lactose monohydrate | 46.25 |
| Hydroxypropyl methyl cellulose (5 Cps) | 25.00 |
| Magnesium stearate | 2.50 |
| Aerosil | 1.25 |
| Total | 232.50 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 2.

TABLE 2

Composition of the coated tablet

| Coated tablet composition | Weight (mg) |
| --- | --- |
| Core tablet | 232.50 |
| Graft copolymer | 17.50 |
| Di-n-butyl phthalate | 1.75 |
| Total | 251.75 |

(II) Dissolution of Diclofenac Sodium

The dissolution of diclofenac sodium was carried out by USP paddle method at 50 rpm. The tablet was exposed to 900 ml of 0.1 N HCl for the first two hours followed by pH 6.8 phosphate buffer solution. The dissolution data of diclofenac sodium is given in Table 3.

TABLE 3

Dissolution of diclofenac sodium

| Time (hrs.) | 1.0 | 2.0 | 3.0 | 4.0 | 5.0 | 6.0 | 7.0 | 8.0 | 9.0 |
| --- | --- | --- | --- | --- | --- | --- | --- | --- | --- |
| % Dissolved (cumulative) | 3.04 | 4.56 | 12.17 | 28.16 | 52.52 | 79.17 | 94.41 | 97.47 | 99.00 |

EXAMPLE 2

This example describes the preparation and the dissolution profile of sustained release diclofenac sodium tablet comprising the pH sensitive graft copolymer

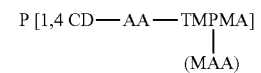

in the core and coat wherein the MAA content is 35 wt. %.

(I) Preparation of Sustained Release Tablet (a) Preparation of Core Tablet

The drug diclofenac sodium, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 8.0 mm in diameter. The composition of tablet is given in Table 4.

TABLE 4

Composition of diclofenac sodium sustained release tablet

| Core tablet composition | Weight (mg) |
| --- | --- |
| Diclofenac sodium | 100.00 |
| Graft copolymer | 57.50 |
| Lactose monohydrate | 46.25 |
| Hydroxypropyl methyl cellulose (5 Cps) | 25.00 |
| Magnesium stearate | 2.50 |
| Aerosil | 1.25 |
| Total | 232.50 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 5.

TABLE 5

Composition of the coated tablet

| Coated tablet composition | Weight (mg) |
| --- | --- |
| Core tablet | 232.50 |
| Graft copolymer | 17.50 |
| Di-n-butyl phthalate | 1.75 |
| Total | 251.75 |

(II) Dissolution of Diclofenac Sodium

The dissolution of diclofenac sodium was carried out by USP paddle method at 50 rpm. The tablet was exposed to 900 ml of 0.1 N HCl for the first two hours followed by pH 6.8 phosphate buffer solution. The dissolution data of diclofenac sodium is given in Table 6.

TABLE 6

| | Dissolution of diclofenac sodium | | | | | | | |
|---|---|---|---|---|---|---|---|---|
| Time (hrs.) | 1.0 | 2.0 | 3.0 | 5.0 | 7.0 | 9.0 | 11.0 | 13.0 | 15.0 |
| % Dissolved (cumulative) | 4.56 | 5.32 | 6.09 | 32.73 | 54.05 | 71.57 | 85.29 | 94.42 | 96.71 |

EXAMPLE 3

This example describes the preparation and the dissolution profile of sustained release diclofenac sodium tablet comprising the pH sensitive graft copolymer

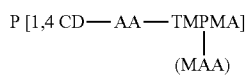

in the core and coat wherein the MAA content is 42 wt. %.

(I) Preparation of Sustained Release Tablet
(a) Preparation of Core Tablet

The drug diclofenac sodium, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 8.0 mm in diameter. The composition of tablet is given in Table 7.

TABLE 7

| Composition of diclofenac sodium sustained release tablet | |
|---|---|
| Core tablet composition | Weight (mg) |
| Diclofenac sodium | 100.00 |
| Graft copolymer | 57.50 |
| Lactose monohydrate | 46.25 |
| Hydroxypropyl methyl cellulose (5 Cps) | 25.00 |
| Magnesium stearate | 2.50 |
| Aerosil | 1.25 |
| Total | 232.50 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 8.

TABLE 8

| Composition of the coated tablet | |
|---|---|
| Coated tablet composition | Weight (mg) |
| Core tablet | 232.50 |
| Graft copolymer | 17.50 |

TABLE 8-continued

| Composition of the coated tablet | |
|---|---|
| Coated tablet composition | Weight (mg) |
| Di-n-butyl phthalate | 1.75 |
| Total | 251.75 |

(II) Dissolution of Diclofenac Sodium

The dissolution of diclofenac sodium was carried out by USP paddle method at 50 rpm.

The tablet was exposed to 900 ml of 0.1 N HCl for the first two hours followed by pH 6.8 phosphate buffer solution. The dissolution data of diclofenac sodium is given in Table 9.

TABLE 9

| | Dissolution of diclofenac sodium | | | | | | | | | |
|---|---|---|---|---|---|---|---|---|---|---|
| Time (hrs.) | 1.0 | 2.0 | 3.0 | 4.0 | 5.0 | 6.0 | 7.0 | 8.0 | 9.0 | 10.0 |
| % Dissolved (cumulative) | 2.28 | 3.04 | 9.13 | 32.72 | 59.37 | 70.81 | 81.47 | 86.81 | 92.90 | 94.43 |

EXAMPLE 4

This example describes the preparation and the dissolution profile of sustained release diclofenac sodium tablet comprising the pH sensitive graft copolymer

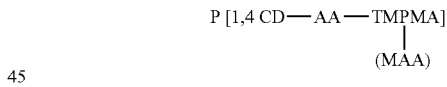

in the core and coat wherein the MAA content is 47 wt. %.

(I) Preparation of Sustained Release Tablet
(a) Preparation of Core Tablet

The drug diclofenac sodium, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 8.0 mm in diameter. The composition of tablet is given in Table 10.

TABLE 10

| Composition of diclofenac sodium sustained release tablet | |
|---|---|
| Core tablet composition | Weight (mg) |
| Diclofenac sodium | 100.00 |
| Graft copolymer | 57.50 |
| Lactose monohydrate | 46.25 |
| Hydroxypropyl methyl cellulose (5 Cps) | 25.00 |
| Magnesium stearate | 2.50 |

TABLE 10-continued

Composition of diclofenac sodium sustained release tablet

| Core tablet composition | Weight (mg) |
| --- | --- |
| Aerosil | 1.25 |
| Total | 232.50 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 11.

TABLE 11

Composition of the coated tablet

| Coated tablet composition | Weight (mg) |
| --- | --- |
| Core tablet | 232.50 |
| Graft copolymer | 17.50 |
| Di-n-butyl phthalate | 1.75 |
| Total | 251.75 |

(II) Dissolution of Diclofenac Sodium

The dissolution of diclofenac sodium was carried out by USP paddle method at 50 rpm. The tablet was exposed to 900 ml of 0.1 N HCl for the first two hours followed by pH 6.8 phosphate buffer solution. The dissolution data of diclofenac sodium is given in Table 12.

TABLE 12

Dissolution of diclofenac sodium

| Time (hrs.) | 1.0 | 2.0 | 3.0 | 4.0 | 5.0 | 6.0 | 7.0 | 8.0 |
| --- | --- | --- | --- | --- | --- | --- | --- | --- |
| % Dissolved (cumulative) | 1.52 | 3.04 | 15.97 | 42.61 | 74.59 | 88.32 | 94.42 | 96.71 |

EXAMPLE 5

This example describes the preparation and the dissolution profile of sustained release diltiazem hydrochloride tablet comprising the pH sensitive graft copolymer

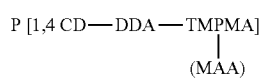

in the core and coat wherein the MAA content is 36 wt. %.

(I) Preparation of Sustained Release Tablet (a) Preparation of Core Tablet

The drug diltiazem hydrochloride, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 13.0 mm in diameter. The composition of tablet is given in Table 13.

TABLE 13

Composition of diltiazem hydrochloride sustained release tablet

| Core tablet composition | Weight (mg) |
| --- | --- |
| Diltiazem hydrochloride | 240.00 |
| Graft copolymer | 198.00 |
| Lactose monohydrate | 81.00 |
| Hydroxypropyl methyl cellulose (5 Cps) | 30.00 |
| Magnesium stearate | 6.00 |
| Aerosil | 3.00 |
| Total | 558.00 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 14.

TABLE 14

Composition of the coated tablet

| Coated tablet composition | Weight (mg) |
| --- | --- |
| Core tablet | 558.00 |
| Graft copolymer | 42.00 |
| Di-n-butyl phthalate | 4.20 |
| Total | 604.20 |

(II) Dissolution of Diltiazem Hydrochloride

The dissolution of diltiazem hydrochloride was carried out by USP paddle method at 50 rpm. The tablet was exposed to 900 ml of 0.1 N HCl for the first two hours followed by pH 6.8 phosphate buffer solution. The dissolution data of diltiazem hydrochloride is given in Table 15.

TABLE 15

Dissolution of diltiazem hydrochloride

| Time (hrs.) | 1.0 | 2.0 | 3.0 | 5.0 | 7.0 | 9.0 | 11.0 | 13.0 | 15.0 | 17.0 |
| --- | --- | --- | --- | --- | --- | --- | --- | --- | --- | --- |
| % Dissolved (cumulative) | 0.58 | 0.78 | 4.70 | 13.34 | 35.72 | 60.47 | 79.33 | 92.69 | 96.62 | 98.59 |

EXAMPLE 6

This example describes the preparation and the dissolution profile of sustained release diltiazem hydrochloride tablet comprising the pH sensitive graft copolymer

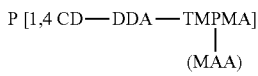

in the core and coat wherein the MAA content is 41 wt. %.

(I) Preparation of Sustained Release Tablet (a) Preparation of Core Tablet

The drug diltiazem hydrochloride, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 13.0 mm in diameter. The composition of tablet is given in Table 16.

TABLE 16

Composition of diltiazem hydrochloride sustained release tablet

| Core tablet composition | Weight (mg) |
| --- | --- |
| Diltiazem hydrochloride | 240.00 |
| Graft copolymer | 198.00 |
| Lactose monohydrate | 81.00 |
| Hydroxypropyl methyl cellulose (5 Cps) | 30.00 |
| Magnesium stearate | 6.00 |
| Aerosil | 3.00 |
| Total | 558.00 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 17.

TABLE 17

Composition of the coated tablet

| Coated tablet composition | Weight (mg) |
| --- | --- |
| Core tablet | 558.00 |
| Graft copolymer | 42.00 |
| Di-n-butyl phthalate | 4.20 |
| Total | 604.20 |

(II) Dissolution of Diltiazem Hydrochloride

The dissolution of diltiazem hydrochloride was carried out by USP paddle method at 50 rpm. The tablet was exposed to 900 ml of 0.1 N HCl for the first two hours followed by pH 6.8 phosphate buffer solution. The dissolution data of diltiazem hydrochloride is given in Table 18.

TABLE 18

Dissolution of diltiazem hydrochloride

| Time (hrs.) | 1.0 | 2.0 | 3.0 | 5.0 | 7.0 | 9.0 | 11.0 | 13.0 |
| --- | --- | --- | --- | --- | --- | --- | --- | --- |
| % Dissolved (cumulative) | 2.15 | 2.55 | 7.45 | 24.34 | 63.61 | 84.24 | 94.06 | 98.39 |

EXAMPLE 7

This example describes the preparation and the dissolution profile of sustained release diltiazem hydrochloride tablet comprising the pH sensitive graft copolymer

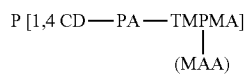

in the core and coat wherein the MAA content is 35 wt. %.

(I) Preparation of Sustained Release Tablet (a) Preparation of Core Tablet

The drug diltiazem hydrochloride, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 13.0 mm in diameter. The composition of tablet is given in Table 19.

TABLE 19

Composition of diltiazem hydrochloride sustained release tablet

| Core tablet composition | Weight (mg) |
| --- | --- |
| Diltiazem hydrochloride | 240.00 |
| Graft copolymer | 198.00 |
| Lactose monohydrate | 81.00 |
| Hydroxypropyl methyl cellulose (5 Cps) | 30.00 |
| Magnesium stearate | 6.00 |
| Aerosil | 3.00 |
| Total | 558.00 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 20.

TABLE 20

Composition of the coated tablet

| Coated tablet composition | Weight (mg) |
| --- | --- |
| Core tablet | 558.00 |
| Graft copolymer | 42.00 |
| Di-n-butyl phthalate | 4.20 |
| Total | 604.20 |

(II) Dissolution of Diltiazem Hydrochloride

The dissolution of diltiazem hydrochloride was carried out by USP paddle method at 50 rpm. The tablet was exposed to 900 ml of 0.1 N HCl for the first two hours followed by pH 6.8 phosphate buffer solution. The dissolution data of diltiazem hydrochloride is given in Table 21.

TABLE 21

Dissolution of diltiazem hydrochloride

| Time (hrs.) | 1.0 | 2.0 | 3.0 | 5.0 | 7.0 | 9.0 | 11.0 | 13.0 | 15.0 | 17.0 |
|---|---|---|---|---|---|---|---|---|---|---|
| % Dissolved (cumulative) | 1.37 | 1.76 | 3.33 | 9.42 | 17.86 | 32.59 | 55.37 | 71.87 | 86.20 | 95.44 |

EXAMPLE 8

This example describes the preparation and the dissolution profile of sustained release diltiazem hydrochloride tablet comprising the pH sensitive graft copolymer

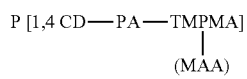

in the core and coat wherein the MAA content is 43 wt. %.

(I) Preparation of Sustained Release Tablet (a) Preparation of Core Tablet

The drug diltiazem hydrochloride, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 13.0 mm in diameter. The composition of tablet is given in Table 22.

TABLE 22

Composition of diltiazem hydrochloride sustained release tablet

| Core tablet composition | Weight (mg) |
|---|---|
| Diltiazem hydrochloride | 240.00 |
| Graft copolymer | 198.00 |
| Lactose monohydrate | 81.00 |
| Hydroxypropyl methyl cellulose (5 Cps) | 30.00 |
| Magnesium stearate | 6.00 |
| Aerosil | 3.00 |
| Total | 558.00 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 23.

TABLE 23

Composition of the coated tablet

| Coated tablet composition | Weight (mg) |
|---|---|
| Core tablet | 558.00 |
| Graft copolymer | 42.00 |
| Di-n-butyl phthalate | 4.20 |
| Total | 604.20 |

(II) Dissolution of Diltiazem Hydrochloride

The dissolution of diltiazem hydrochloride was carried out by USP paddle method at 50 rpm. The tablet was exposed to 900 ml of 0.1 N HCl for the first two hours followed by pH 6.8 phosphate buffer solution. The dissolution data of diltiazem hydrochloride is given in Table 24.

TABLE 24

Dissolution of diltiazem hydrochloride

| Time (hrs.) | 1.0 | 2.0 | 3.0 | 5.0 | 7.0 | 9.0 | 11.0 | 13.0 |
|---|---|---|---|---|---|---|---|---|
| % Dissolved (cumulative) | 2.15 | 2.94 | 7.06 | 21.98 | 55.36 | 82.66 | 97.40 | 99.37 |

EXAMPLE 9

This example describes the preparation and the dissolution profile of sustained release diltiazem hydrochloride tablet comprising the pH sensitive graft copolymer

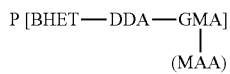

in the core and coat wherein the MAA content is 34 wt. %.

(I) Preparation of Sustained Release Tablet (a) Preparation of Core Tablet

The drug diltiazem hydrochloride, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 13.0 mm in diameter. The composition of tablet is given in Table 25.

TABLE 25

Composition of diltiazem hydrochloride sustained release tablet

| Core tablet composition | Weight (mg) |
|---|---|
| Diltiazem hydrochloride | 240.00 |
| Graft copolymer | 198.00 |
| Lactose monohydrate | 81.00 |
| Hydroxypropyl methyl cellulose (5 Cps) | 30.00 |
| Magnesium stearate | 6.00 |
| Aerosil | 3.00 |
| Total | 558.00 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 26.

TABLE 26

Composition of the coated tablet

| Coated tablet composition | Weight (mg) |
|---|---|
| Core tablet | 558.00 |
| Graft copolymer | 42.00 |

TABLE 26-continued

| Composition of the coated tablet | |
|---|---|
| Coated tablet composition | Weight (mg) |
| Di-n-butyl phthalate | 4.20 |
| Total | 604.20 |

(II) Dissolution of Diltiazem Hydrochloride

The dissolution of diltiazem hydrochloride was carried out by USP paddle method at 50 rpm. The tablet was exposed to 900 ml of 0.1 N HCl for the first two hours followed by pH 6.8 phosphate buffer solution. The dissolution data of diltiazem hydrochloride is given in Table 27.

TABLE 27

| Dissolution of diltiazem hydrochloride | | | | | | | | | |
|---|---|---|---|---|---|---|---|---|---|
| Time (hrs.) | 1.0 | 2.0 | 3.0 | 5.0 | 7.0 | 9.0 | 11.0 | 13.0 | 15.0 | 17.0 |
| % Dissolved (cumulative) | 0.39 | 0.58 | 3.33 | 10.99 | 25.91 | 41.62 | 58.12 | 72.06 | 84.83 | 95.05 |

EXAMPLE 10

This example describes the preparation and the dissolution profile of sustained release theophylline tablet comprising the pH sensitive graft copolymer

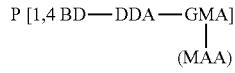

in the core and coat wherein the MAA content is 34 wt. %.
(I) Preparation of Sustained Release Tablet
(a) Preparation of Core Tablet The drug theophylline, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 8.0 mm in diameter. The composition of tablet is given in Table 28.

TABLE 28

| Composition of theophylline sustained release tablet | |
|---|---|
| Core tablet composition | Weight (mg) |
| Theophylline | 75.00 |
| Graft copolymer | 95.00 |
| Lactose monohydrate | 33.75 |
| Hydroxypropyl methyl cellulose (5 Cps) | 25.00 |
| Magnesium stearate | 2.50 |
| Aerosil | 1.25 |
| Total | 232.50 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 29.

TABLE 29

| Composition of the coated tablet | |
|---|---|
| Coated tablet composition | Weight (mg) |
| Core tablet | 232.50 |
| Graft copolymer | 17.50 |

TABLE 29-continued

| Composition of the coated tablet | |
|---|---|
| Coated tablet composition | Weight (mg) |
| Di-n-butyl phthalate | 1.75 |
| Total | 251.75 |

(II) Dissolution of Theophylline

The dissolution of theophylline was carried out by USP paddle method at 50 rpm. The tablet was exposed to 900 ml of 0.1 N HCl for the first two hours followed by pH 6.8 phosphate buffer solution. The dissolution data of theophylline is given in Table 30.

TABLE 30

| Dissolution of theophylline | | | | | | | | | |
|---|---|---|---|---|---|---|---|---|---|
| Time (hrs.) | 1.0 | 2.0 | 3.0 | 5.0 | 7.0 | 9.0 | 11.0 | 13.0 | 15.0 | 17.0 |
| % Dissolved (cumulative) | 0.66 | 0.66 | 2.66 | 13.35 | 34.72 | 57.43 | 72.13 | 84.82 | 92.17 | 95.51 |

EXAMPLE 11

This example describes the preparation and the dissolution profile of sustained release theophylline tablet comprising the pH sensitive graft copolymer

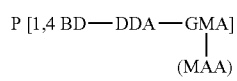

in the core and coat wherein the MAA content is 44 wt. %.
(I) Preparation of Sustained Release Tablet
(a) Preparation of Core Tablet The drug theophylline, pH sensitive graft copolymer, lactose monohydrate and hydroxylpropyl methyl cellulose (5

Cps) were dry granulated. To this magnesium stearate and aerosil were added and mixed thoroughly. The granular mixture was compressed into tablet 8.0 mm in diameter. The composition of tablet is given in Table 31.

TABLE 31

Composition of theophylline sustained release tablet

| Core tablet composition | Weight (mg) |
| --- | --- |
| Theophylline | 150.00 |
| Graft copolymer | 45.00 |
| Lactose monohydrate | 21.25 |
| Hydroxypropyl methyl cellulose (5 Cps) | 12.50 |
| Magnesium stearate | 2.50 |
| Aerosil | 1.25 |
| Total | 232.50 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 32.

TABLE 32

Composition of the coated tablet

| Coated tablet composition | Weight (mg) |
| --- | --- |
| Core tablet | 232.50 |
| Graft copolymer | 17.50 |
| Di-n-butyl phthalate | 1.75 |
| Total | 251.75 |

(II) Dissolution of Theophylline

The dissolution of theophylline was carried out by USP paddle method at 50 rpm. The tablet was exposed to 900 ml of 0.1 N HCl for the first two hours followed by pH 6.8 phosphate buffer solution. The dissolution data of theophylline is given in Table 33.

TABLE 33

Dissolution of theophylline

| Time (hrs.) | 1.0 | 2.0 | 3.0 | 4.0 | 5.0 | 6.0 | 7.0 | 8.0 | 9.0 | 10.0 |
| --- | --- | --- | --- | --- | --- | --- | --- | --- | --- | --- |
| % Dissolved (cumulative) | 0.33 | 0.66 | 12.01 | 37.36 | 52.04 | 73.72 | 82.73 | 92.07 | 94.74 | 97.75 |

EXAMPLE 12

This example describes the preparation and the dissolution profile of sustained release theophylline tablet comprising the pH sensitive graft copolymer

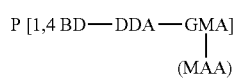

in the core and coat wherein the MAA content is 44 wt. %.
(I) Preparation of Sustained Release Tablet
(a) Preparation of Core Tablet The drug theophylline, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 8.0 mm in diameter. The composition of tablet is given in Table 34.

TABLE 34

Composition of theophylline sustained release tablet

| Core tablet composition | Weight (mg) |
| --- | --- |
| Theophylline | 175.00 |
| Graft copolymer | 32.50 |
| Lactose monohydrate | 15.00 |
| Hydroxypropyl methyl cellulose (5 Cps) | 7.50 |
| Magnesium stearate | 2.00 |
| Aerosil | 0.50 |
| Total | 232.50 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 35.

TABLE 35

Composition of the coated tablet

| Coated tablet composition | Weight (mg) |
| --- | --- |
| Core tablet | 232.50 |
| Graft copolymer | 17.50 |
| Di-n-butyl phthalate | 1.75 |
| Total | 251.75 |

(II) Dissolution of Theophylline

The dissolution of theophylline was carried out by USP paddle method at 50 rpm. The tablet was exposed to 900 ml of 0.1 N HCl for the first two hours followed by pH 6.8 phosphate buffer solution. The dissolution data of theophylline is given in Table 36.

TABLE 36

Dissolution of theophylline

| Time (hrs.) | 1.0 | 2.0 | 3.0 | 4.0 | 5.0 | 6.0 | 7.0 | 8.0 |
| --- | --- | --- | --- | --- | --- | --- | --- | --- |
| % Dissolved (cumulative) | 0.28 | 0.57 | 13.15 | 39.47 | 76.10 | 92.73 | 96.75 | 98.47 |

EXAMPLE 13

This example describes the preparation and the dissolution profile of sustained release acetaminophen tablet comprising the pH sensitive graft copolymer

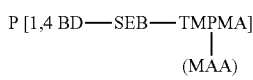

in the core and coat wherein the MAA content is 34 wt. %.

(I) Preparation of Sustained Release Tablet
(a) Preparation of Core Tablet

The drug acetaminophen, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 8.0 mm in diameter. The composition of tablet is given in Table 37.

TABLE 37

Composition of acetaminophen sustained release tablet

| Core tablet composition | Weight (mg) |
| --- | --- |
| Acetaminophen | 75.00 |
| Graft copolymer | 129.00 |
| Lactose monohydrate | 40.50 |
| Hydroxypropyl methyl cellulose (5 Cps) | 30.00 |
| Magnesium stearate | 3.00 |
| Aerosil | 1.50 |
| Total | 279.00 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 38.

TABLE 38

Composition of the coated tablet

| Coated tablet composition | Weight (mg) |
| --- | --- |
| Core tablet | 279.00 |
| Graft copolymer | 21.00 |
| Di-n-butyl phthalate | 2.10 |
| Total | 302.10 |

(II) Dissolution of Acetaminophen

The dissolution of acetaminophen was carried out by USP paddle method at 50 rpm.

The tablet was exposed to 900 ml of 0.1 N HCl for the first two hours followed by pH 6.8 phosphate buffer solution. The dissolution data of acetaminophen is given in Table 39.

TABLE 39

Dissolution of acetaminophen

| Time (hrs.) | 1.0 | 2.0 | 3.0 | 5.0 | 7.0 | 9.0 | 11.0 | 13.0 | 15.0 | 17.0 |
| --- | --- | --- | --- | --- | --- | --- | --- | --- | --- | --- |
| % Dissolved (cumulative) | 3.24 | 4.32 | 7.03 | 38.41 | 62.23 | 75.23 | 84.98 | 91.48 | 96.35 | 97.97 |

EXAMPLE 14

This example describes the preparation and the dissolution profile of sustained release acetaminophen tablet comprising the pH sensitive graft copolymer

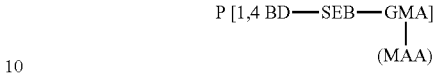

in the core and coat wherein the MAA content is 55 wt. %.
(I) Preparation of Sustained Release Tablet
(a) Preparation of Core Tablet The drug acetaminophen, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 8.0 mm in diameter. The composition of tablet is given in Table 40.

TABLE 40

Composition of acetaminophen sustained release tablet

| Core tablet composition | Weight (mg) |
| --- | --- |
| Acetaminophen | 150.00 |
| Graft copolymer | 54.00 |
| Lactose monohydrate | 40.50 |
| Hydroxypropyl methyl cellulose (5 Cps) | 30.00 |
| Magnesium stearate | 3.00 |
| Aerosil | 1.50 |
| Total | 279.00 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 41.

TABLE 41

Composition of the coated tablet

| Coated tablet composition | Weight (mg) |
| --- | --- |
| Core tablet | 279.00 |
| Graft copolymer | 21.00 |
| Di-n-butyl phthalate | 2.10 |
| Total | 302.10 |

(II) Dissolution of Acetaminophen

The dissolution of acetaminophen was carried out by USP paddle method at 50 rpm. The tablet was exposed to 900 ml of 0.1 N HCl for the first two hours followed by pH 6.8 phosphate buffer solution. The dissolution data of acetaminophen is given in Table 42.

TABLE 42

| Dissolution of acetaminophen | | | | | | | | |
|---|---|---|---|---|---|---|---|---|
| Time (hrs.) | 1.0 | 2.0 | 3.0 | 4.0 | 5.0 | 6.0 | 7.0 | 8.0 |
| % Dissolved (cumulative) | 2.43 | 2.70 | 26.49 | 60.32 | 73.87 | 88.22 | 95.80 | 97.70 |

EXAMPLE 15

This example describes the preparation and the dissolution profile of sustained release acetaminophen tablet comprising the pH sensitive graft copolymer (A)

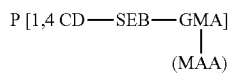

in the core wherein the MAA content is 40 wt. % and the pH sensitive graft copolymer (B)

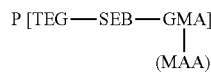

in the coat wherein the MAA content is 48 wt. %.

(I) Preparation of Sustained Release Tablet (a) Preparation of Core Tablet

The drug acetaminophen, pH sensitive graft copolymer (A), lactose monohydrate and hydroxylpropyl methyl cellulose (5 Cps) were dry granulated. To this magnesium stearate and aerosil were added and mixed thoroughly. The granular mixture was compressed into tablet 8.0 mm in diameter. The composition of tablet is given in Table 43.

TABLE 43

| Composition of acetaminophen sustained release tablet | |
|---|---|
| Core tablet composition | Weight (mg) |
| Acetaminophen | 100.00 |
| Graft copolymer (A) | 57.50 |
| Lactose monohydrate | 33.75 |
| Hydroxypropyl methyl cellulose (5 Cps) | 37.50 |
| Magnesium stearate | 2.50 |
| Aerosil | 1.25 |
| Total | 232.50 |

(b) Preparation of Coated Tablet

The pH sensitive graft copolymer (B) and di-n-butyl phthalate were dissolved in solvent mixture (chloroform/methanol, 1:1 v/v) to obtain 10% solution. The core tablet was coated and dried at room temperature. The composition of coated tablet is given in Table 44.

TABLE 44

| Composition of the coated tablet | |
|---|---|
| Coated tablet composition | Weight (mg) |
| Core tablet | 232.50 |
| Graft copolymer (B) | 17.50 |
| Di-n-butyl phthalate | 1.75 |
| Total | 251.75 |

(II) Dissolution of Acetaminophen

The dissolution of acetaminophen was carried out by USP paddle method at 50 rpm. The tablet was exposed to 900 ml of 0.1 N HCl for the first two hours followed by pH 6.8 phosphate buffer solution. The dissolution data of acetaminophen is given in Table 45.

TABLE 45

| Dissolution of acetaminophen | | | | | | | | | |
|---|---|---|---|---|---|---|---|---|---|
| Time (hrs.) | 1.0 | 2.0 | 3.0 | 5.0 | 7.0 | 9.0 | 11.0 | 13.0 | 15.0 |
| % Dissolved (cumulative) | 0.31 | 1.55 | 5.74 | 34.81 | 65.15 | 82.26 | 86.46 | 92.68 | 95.17 |

EXAMPLE 16

This example describes the preparation and the dissolution profile of sustained release cephalexin monohydrate tablet comprising the pH sensitive graft copolymer

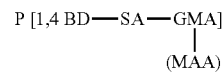

in the core and coat wherein the MAA content is 46 wt. %.

(I) Preparation of Sustained Release Tablet (a) Preparation of Core Tablet

The drug cephalexin monohydrate, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 8.0 mm in diameter. The composition of tablet is given in Table 46.

TABLE 46

Composition of cephalexin monohydrate sustained release tablet

| Core tablet composition | Weight (mg) |
| --- | --- |
| Cephalexin monohydrate | 25.00 |
| Graft copolymer | 82.50 |
| Lactose monohydrate | 75.00 |
| Hydroxypropyl methyl cellulose (5 Cps) | 37.50 |
| Magnesium stearate | 8.75 |
| Aerosil | 3.75 |
| Total | 232.50 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 47.

TABLE 47

Composition of the coated tablet

| Coated tablet composition | Weight (mg) |
| --- | --- |
| Core tablet | 232.50 |
| Graft copolymer | 17.50 |
| Di-n-butyl phthalate | 1.75 |
| Total | 251.75 |

(II) Dissolution of Cephalexin Monohydrate

The dissolution of cephalexin monohydrate was carried out by USP paddle method at 50 rpm. The tablet was exposed to 900 ml of 0.1 N HCl for the first two hours followed by pH 6.8 phosphate buffer solution. The dissolution data of cephalexin monohydrate is given in Table 48.

TABLE 48

Dissolution of cephalexin monohydrate

| Time (hrs.) | 1.0 | 2.0 | 3.0 | 4.0 | 5.0 | 6.0 | 7.0 | 8.0 | 9.0 |
| --- | --- | --- | --- | --- | --- | --- | --- | --- | --- |
| % Dissolved (cumulative) | 2.69 | 5.38 | 21.54 | 48.49 | 64.67 | 80.85 | 86.25 | 91.64 | 97.04 |

EXAMPLE 17

This example describes the preparation and the dissolution profile of sustained release cephalexin monohydrate tablet comprising the pH sensitive graft copolymer

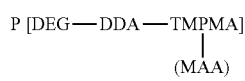

in the core and coat wherein the MAA content is 47 wt. %.

(I) Preparation of Sustained Release Tablet (a) Preparation of Core Tablet

The drug cephalexin monohydrate, pH sensitive graft copolymer, lactose monohydrate and hydroxylpropyl methyl cellulose (5 Cps) were dry granulated. To this magnesium stearate and aerosil were added and mixed thoroughly. The granular mixture was compressed into tablet 8.0 mm in diameter. The composition of tablet is given in Table 49.

TABLE 49

Composition of cephalexin monohydrate sustained release tablet

| Core tablet composition | Weight (mg) |
| --- | --- |
| Cephalexin monohydrate | 25.00 |
| Graft copolymer | 82.50 |
| Lactose monohydrate | 75.00 |
| Hydroxypropyl methyl cellulose (5 Cps) | 37.50 |
| Magnesium stearate | 8.75 |
| Aerosil | 3.75 |
| Total | 232.50 |

(b) Preparation of Coated Tablet

The pH sensitive graft copolymer and di-n-butyl phthalate were dissolved in solvent mixture (chloroform/methanol, 1:1 v/v) to obtain 10% solution. The core tablet was coated and dried at room temperature. The composition of coated tablet is given in Table 50.

TABLE 50

Composition of the coated tablet

| Coated tablet composition | Weight (mg) |
| --- | --- |
| Core tablet | 232.50 |
| Graft copolymer | 17.50 |
| Di-n-butyl phthalate | 1.75 |
| Total | 251.75 |

(II) Dissolution of Cephalexin Monohydrate

The dissolution of cephalexin monohydrate was carried out by USP paddle method at 50 rpm. The tablet was exposed to 900 ml of 0.1 N HCl for the first two hours followed by pH 6.8 phosphate buffer solution. The dissolution data of cephalexin monohydrate is given in Table 51.

TABLE 51

| Dissolution of cephalexin monohydrate | | | | | | | | | | |
|---|---|---|---|---|---|---|---|---|---|---|
| Time (hrs.) | 1.0 | 2.0 | 3.0 | 4.0 | 5.0 | 6.0 | 7.0 | 8.0 | 9.0 | 10.0 |
| % Dissolved (cumulative) | 5.38 | 5.39 | 10.77 | 21.55 | 37.72 | 53.89 | 64.68 | 80.85 | 91.64 | 97.04 |

EXAMPLE 18

This example describes the preparation and the dissolution profile of sustained release acetaminophen tablet comprising the pH sensitive graft copolymer (A)

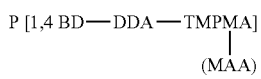

in the core wherein the MAA content is 35 wt. % and the pH sensitive graft copolymer (B)

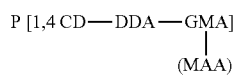

in the coat wherein the MAA content is 49 wt. %.
(I) Preparation of Sustained Release Tablet
(a) Preparation of Core Tablet The drug cephalexin monohydrate, pH sensitive graft copolymer (A), lactose monohydrate and hydroxylpropyl methyl cellulose (5 Cps) were dry granulated. To this magnesium stearate and aerosil were added and mixed thoroughly. The granular mixture was compressed into tablet 8.0 mm in diameter. The composition of tablet is given in Table 52.

TABLE 52

| Composition of cephalexin monohydrate sustained release tablet | |
|---|---|
| Core tablet composition | Weight (mg) |
| Cephalexin monohydrate | 100.00 |
| Graft copolymer (A) | 57.50 |
| Lactose monohydrate | 33.75 |
| Hydroxypropyl methyl cellulose (5 Cps) | 37.50 |
| Magnesium stearate | 2.50 |
| Aerosil | 1.25 |
| Total | 232.50 |

(b) Preparation of Coated Tablet

The pH sensitive graft copolymer (B) and di-n-butyl phthalate were dissolved in solvent mixture (chloroform/methanol, 1:1 v/v) to obtain 10% solution. The core tablet was coated and dried at room temperature. The composition of coated tablet is given in Table 53.

TABLE 53

| Composition of the coated tablet | |
|---|---|
| Coated tablet composition | Weight (mg) |
| Core tablet | 232.50 |
| Graft copolymer (B) | 17.50 |
| Di-n-butyl phthalate | 1.75 |
| Total | 251.75 |

(II) Dissolution of Cephalexin Monohydrate

The dissolution of cephalexin monohydrate was carried out by USP paddle method at 50 rpm. The tablet was exposed to 900 ml of 0.1 N HCl for the first two hours followed by pH 6.8 phosphate buffer solution. The dissolution data of cephalexin monohydrate is given in Table 54.

TABLE 54

| Dissolution of cephalexin monohydrate | | | | | | | | | |
|---|---|---|---|---|---|---|---|---|---|
| Time (hrs.) | 1.0 | 2.0 | 3.0 | 5.0 | 7.0 | 9.0 | 11.0 | 13.0 | 15.0 |
| % Dissolved (cumulative) | 0.70 | 1.26 | 17.12 | 46.22 | 66.74 | 77.70 | 90.07 | 96.96 | 98.79 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

ADVANTAGES OF THE INVENTION

The disclosed formulations suppress the drug release at pH prevalent in the stomach and release over an extended period of time at pH prevalent in the intestinal region.
The disclosed formulations do not require more than one polymer to obtain the release as said above.
The disclosed formulations are useful for the drugs differing in solubility.

We claim:
1. A sustained release composition for oral administration comprising:

a. a graft copolymer which exhibits pH dependent behavior having the formula 1

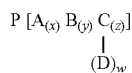

comprising:
i. a backbone having the formula P [A$_{(x)}$B$_{(y)}$C$_{(z)}$] comprising a diol (A), a dicarboxylic acid or acid anhydride (B) and a monomer containing pendent unsaturation (C) wherein (x)=39-46%, (y)=49-54% (z)=5-8% by mole;
ii. a graft which is a polymer of the acidic monomer (D) which comprises 'w' weight percent of the total weight of the said graft copolymer such that 'w' is 34-55%;
b. an orally ingestible therapeutically active agent; and
c. an orally ingestible pharmaceutically acceptable ingredient to form an orally ingestible composition for sustained release of the orally ingestible therapeutically active agent in the gastrointestinal tract of a patient, wherein said orally ingestible composition is in the form of a tablet.

2. The sustained release composition as claimed in claim 1, wherein the backbone is poly (ester-ether) or polyester.

3. The sustained release composition as claimed in claim 1, wherein the diol is selected from the group consisting of aliphatic diol, cycloaliphatic diol and aromatic diol.

4. The sustained release composition as claimed in claim 3, wherein the aliphatic diol is selected from the group consisting of diethylene glycol, triethylene glycol, tetraethylene glycol, dipropylene glycol, tripropylene glycol, polyethylene glycol (M$_n$~200), polyethylene glycol (M$_n$~400), polyethylene glycol (M$_n$~1000), polyethylene glycol (M$_n$~2000), 1,2-ethane diol, 1,3-propane diol, 1,2-propane diol, 2-methyl-1,3-propane diol, 1,4-butane diol, 1,3-butane diol, 1,2-butane diol, 1,5-pentane diol, 1,6-hexane diol, 1,7-heptane diol, 1,8-octane diol, 1,9-nonane diol and 1,12-dodecane diol.

5. The sustained release composition as claimed in claim 3, wherein the cycloaliphatic diol is 1,4-cyclohexanedimethanol.

6. The sustained release composition as claimed in claim 3, wherein the aromatic diol is bis(2-hydroxyethyl) terephthalate.

7. The sustained release composition as claimed in claim 1, wherein the dicarboxylic acid is selected from the group consisting of succinic acid, glutaric acid, adipic acid, pimelic acid, suberic acid, azelaic acid, sebacic acid and dodecanedioic acid.

8. The sustained release composition as claimed in claim 1, wherein the acid anhydride is selected from succinic anhydride and phthalic anhydride.

9. The sustained release composition as claimed in claim 1, wherein the monomer containing pendent unsaturation is an epoxy monomer or a diol monomer.

10. The sustained release composition as claimed in claim 9, wherein the epoxy monomer is selected from glycidyl methacrylate and glycidyl acrylate.

11. The sustained release composition as claimed in claim 9, wherein the diol monomer is selected from trimethylolpropane monomethacrylate and trimethylolpropane monoacrylate.

12. The sustained release composition as claimed in claim 1, wherein the acidic monomer is a carboxylic acid selected from acrylic acid and methacrylic acid.

13. The sustained release composition as claimed in claim 1, wherein the orally ingestible therapeutically active agent is selected from the group consisting of anti-inflammatory drugs, cardiovascular drugs, antibiotic drugs, analgesic drugs and anti-asthmatic drugs.

14. The sustained release composition as claimed in claim 13, wherein the anti-inflammatory drug is selected from the group consisting of ibuprofen, ketoprofen, indomethacin, diclofenac and naproxen.

15. The sustained release composition as claimed in claim 13, wherein the cardiovascular drug is selected from the group consisting of verapamil, nifedepine, captopril, propranolol, atenolol and diltiazem.

16. The sustained release composition as claimed in claim 13, wherein the antibiotic drug is selected from ampicillin and cephalexin.

17. The sustained release composition as claimed in claim 13, wherein the analgesic drug is selected from the group consisting of acetylsalicylic acid, acetaminophen, oxycodone and morphine.

18. The sustained release composition as claimed in claim 13, wherein the anti-asthmatic drug is selected from the group consisting of aminophylline, theophylline and salbutamol.

19. The sustained release composition as claimed in claim 1, wherein the orally ingestible pharmaceutically acceptable ingredient is selected from the group consisting of filler, binder, lubricant and glidant.

20. The sustained release composition as claimed in claim 19, wherein filler is selected from microcrystalline cellulose and lactose monohydrate, binder is selected from hydroxypropyl methyl cellulose and polyvinylpyrrolidone, lubricant is selected from magnesium stearate and talc and glidant is aerosil.

21. The sustained release composition as claimed in claim 1, wherein the pH sensitive graft copolymer comprises 20-50% of the total weight of the formulation.

22. The sustained release composition as claimed in claim 1, wherein the orally ingestible therapeutically active agent comprises 20-40% of the total weight of the formulation.

23. The sustained release composition as claimed in claim 1, wherein the orally ingestible pharmaceutically acceptable ingredients comprise 15-40% of the total weight of the formulation.

24. The sustained release composition as claimed in claim 1, wherein the orally ingestible pharmaceutically acceptable ingredients comprise filler 10-30%, binder 5-10%, lubricant 0.5-2% and glidant 0.2-1% of the total weight of the formulation.

25. The sustained release composition as claimed in claim 1, wherein the orally ingestible sustained release composition is produced in pharmaceutical solid dosage form.

26. The sustained release composition as claimed in claim 25, wherein the dosage form comprises an optional coat of said pH sensitive graft copolymer.

27. The sustained release composition as claimed in claim 1, wherein process for the preparation of the composition comprises the steps of:
I. dry granulating and mixing the orally ingestible therapeutically active agent, pH sensitive graft copolymer and orally ingestible pharmaceutically acceptable ingredient to obtain a granular mixture;
II. compressing the granular mixture obtained in step (I) into a tablet to obtain core tablet;

III. dissolving a pH sensitive graft copolymer and di-n-butyl phthalate in a solvent mixture to obtain a 10% solution;
IV. coating the core tablet obtained in step (II) with the 10% solution of the pH sensitive graft copolymer and di-n-butyl phthalate obtained in step (III) to obtain a coated tablet; and
V. drying the coated tablet obtained in step (IV) to obtain an orally ingestible sustained release composition.

* * * * *